United States Patent [19]

Winterbourn et al.

[11] Patent Number: Plant 7,030

[45] Date of Patent: Sep. 12, 1989

[54] PHILODENDRON WINTERBOURN

[76] Inventors: Veronica L. Winterbourn; Barry M. Winterbourn, both of PO Box 12, Gosnells, Australia

[21] Appl. No.: 145,499

[22] Filed: Jan. 19, 1988

[30] Foreign Application Priority Data

Jan. 19, 1987 [AU] Australia ..... PH9932

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Harness, Dickey & Pierce

[57] ABSTRACT

A cultivar of Philodendron Selloum having more and smaller leaves, with a red spadix.

3 Drawing Sheets

The present invention relates to a new and distinct variety of Philodendron which is believed to be a sport of the Philodendron Selloum. The plant was grown from a seed found in a collection of seeds from the Philodendron Selloum and is believed to be derived from that variety. The denomination of this new variety is "Philodendron Winterbourn".

Among the novel characteristics distinguishing this variety from Philodendron Selloum is that the new variety is a smaller leaved much more compact plant than Philodendron Selloum generally having many more leaves than similar aged plants of Philodendron Selloum. While the leaves of Philodendron Winterbourn are similar in overall morphology to those of Philodendron Selloum, they differ markedly in their size. The leaves of Philodendron Winterbourn are approximately three-fourths the length of those of Philodendron Selloum, but only one-third the breadth. That is, while the leaves of Philodendron Selloum are nearly as broad at the base as they are long, the leaves of Philodendron Winterbourn are only slightly over half as wide at the base as they are long. The veins on the back of the leaves of Philodendron Selloum also apparently do not turn reddish as they do in older plants of Philodendron Winterbourn. The spathe of Philodendron Selloum is green on the outside whereas that of Philodendron Winterbourn is a dull, dark red.

The accompanying drawings are photographs showing the vegetation and flower of the new variety as depicted in color as nearly as true as reasonably possible to make the same in a photograph of this character.

The following is a detailed description of the new variety:

A cultivar which results in the following characteristic:

Height: Shrub to about 1 meter tall.

Stem: Few branched, internodes not developed, the sixty or more leaves forming a dense crown, the leaf scars crowded together on the stem.

Leaf size: About 12 to 20 centimeters across and 22 to 35 centimeters long.

Leaf characteristics: Leaf blades ovate to narrow-ovate (with the base often truncated) in outline and the tip (terminal lobe) sometimes acuminate, almost flat or V-shaped, especially at the sinus, margins slightly recurved, pinnatifid, with five to eight pairs of lobes, the younger leaves divided half-way to the midrib (and with the fewer lobes) and the older leaves divided to three-fourths of the way to the midrib or more; terminal and side lobes tapering on younger leaves, side lobes nearly parallel sided on older leaves and slightly curved towards the terminal lobe, terminal lobe poorly separated from adjacent lobes, especially on younger leaves, lobes angled forward at about 50 degress from the midrib, obtuse to acute; basal lobes bipinnatifid, the secondary lobes all poorly developed (or missing) except the secondary basal lobe away from the sinus (the one towards the sinus is missing), mature leaves dark green (27E8 to 27F8 to 27F7), glossy, with light-green (28A5 to 28A6) midrib and major veins on the adaxial surface and reddish (10CT) major veins and midrib on the abaxial surface. Major veins sub-opposite to alternate.

Flower: The peduncle is a dull olive green (2C5 to 2D5), transition to the spathe is oblique and abrupt. The spathe is c. 12 cm long and uniformly c. 3.5 cm diameter with a small point at the top. The outside of the spathe is smooth and shiny, it is a dull dark red (11C8 to 11D8), suffused with green towards the base and somewhat lighter (11B7) toward the apex. The inside of the spathe is dull, the lower half is pale pink (11A3 to 11A4) and the upper half is cream-colored (4A2 to 4A3). The spadix has cream colored (4A2 to 4A3) flowers over the upper four-fifths of its length and pale yellow (2A4 to 2A5) female flowers over the lower fifth. Its surface is pink (11A4 to 11A5) in the lower two-thirds and cream colored (4A2 to 4A3) in the upper third.

I claim:

1. A new and distinct variety of Philodendron substantially as shown and described characterized by a more compact plant having more leaves that are only slightly half as wide at the base as they are long with a spathe of a dull dark red color and a flower characterized by a peduncle of a dull olive green color with the transition to the spathe being obliquely and abrupt and flowers are cream colored for the upper four-fifths of their length and have pale yellow female flowers over the lower fifth, the surface is pink in the lower two-thirds and cream colored in the upper third.

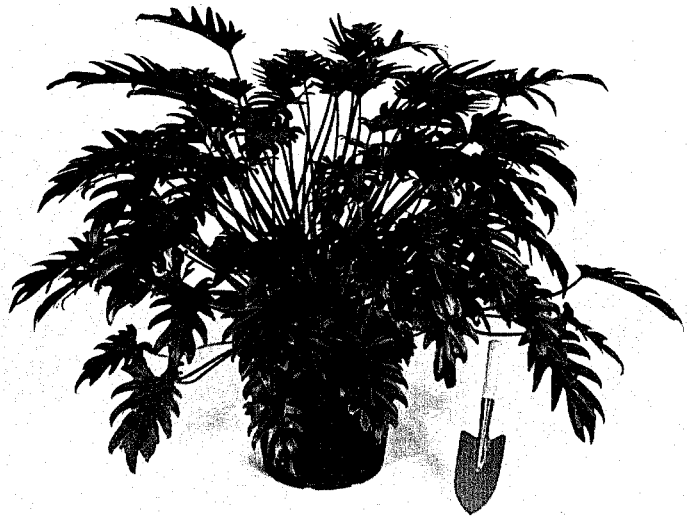

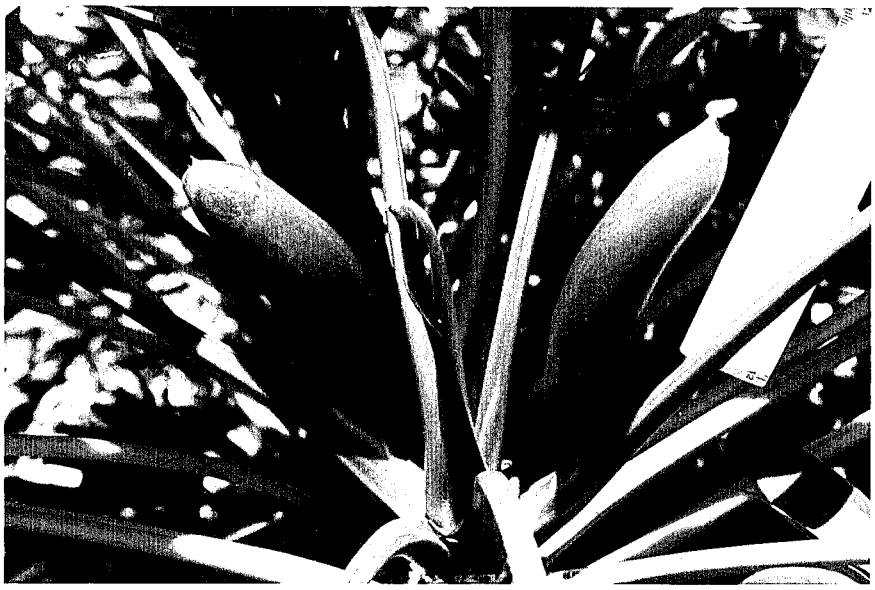

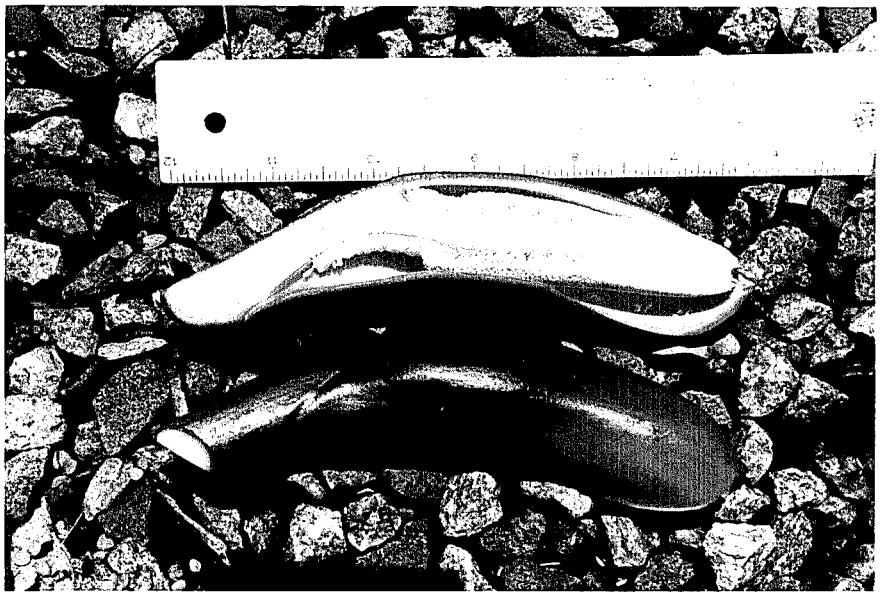

* * * * *